United States Patent

Blaser et al.

[11] 4,335,054
[45] Jun. 15, 1982

[54] PROCESS FOR THE PREPARATION OF ALKENYLBENZENECARBOXYLIC ACID DERIVATIVES AND ALKENYLNAPHTHALENECARBOXYLIC ACID DERIVATIVES

[75] Inventors: Hans-Ulrich Blaser, Ettingen, Switzerland; Dieter Reinehr, Kandern, Fed. Rep. of Germany; Alwyn Spencer, Basel, Switzerland

[73] Assignee: Ciba-Geigy Corporation, Ardsley, N.Y.

[21] Appl. No.: 262,000

[22] Filed: May 8, 1981

[30] Foreign Application Priority Data

May 13, 1980 [CH] Switzerland .................. 3732/80

[51] Int. Cl.³ .................. C07C 121/70; C07C 49/217; C07C 69/618; C07C 103/22
[52] U.S. Cl. .............................. 260/465 G; 549/452; 260/465 D; 549/454; 549/451; 260/465 E; 260/465 F; 260/465 H; 260/465 K; 560/10; 560/1; 560/19; 560/20; 560/21; 560/51; 560/55; 560/56; 560/80; 560/81; 560/82; 560/100; 560/102; 560/104; 564/156; 564/162; 564/163; 564/166; 564/169; 564/170; 564/172; 564/180; 564/182; 568/306; 568/316; 549/373; 549/375
[58] Field of Search .......... 260/465 D, 465 F, 465 G, 260/465 H, 564 K; 560/20, 51, 55, 80, 81, 82, 100, 102, 104; 564/166, 170, 180, 182; 568/316

[56] References Cited

U.S. PATENT DOCUMENTS 3,922,299  11/1975  Heck .................................. 560/104

FOREIGN PATENT DOCUMENTS 1536480  12/1978  United Kingdom .

OTHER PUBLICATIONS

Biavati et al., Transition Met. Chem., vol. 4, pp. 398-399 (1979).
Tohde et al., Synthesis, Nov. 1977, pp. 777-778 (1977).
Chiusoli et al., Transition Met. Chem., vol. 2, pp. 270-272 (1977).

*Primary Examiner*—Dolph H. Torrence
*Attorney, Agent, or Firm*—Michael W. Glynn

[57] ABSTRACT

Compounds of the formula I

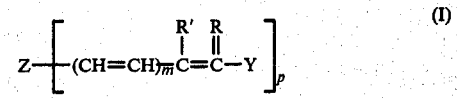

in which p, m, Z, R, R' and Y are as defined in claim 1, can be obtained in a simple and economical manner by a novel process which comprises reacting a halide of the formula

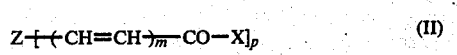

with the corresponding acrylic acid derivative, in the presence of a base and of certain palladium catalysts, such as palladium acetate. The compounds (I), and functional derivatives prepared therefrom, are useful for the preparation of photocrosslinkable polymers, which can in particular be employed as (so-called) photoresists.

12 Claims, No Drawings

PROCESS FOR THE PREPARATION OF ALKENYLBENZENECARBOXYLIC ACID DERIVATIVES AND ALKENYLNAPHTHALENECARBOXYLIC ACID DERIVATIVES

The present invention relates to a novel process for the preparation of alkenylbenzenecarboxylic acid derivatives and alkenylnaphthalenecarboxylic acid derivatives.

U.S. Pat. No. 3,922,299 discloses that vinyl-substituted or allyl-substituted organic compounds, in particular cinnamic acid and cinnamic acid esters, can be prepared by catalytic reaction of a corresponding halide with an activated olefin, such as methyl acrylate, in the presence of a tertiary amine. The preferred catalysts are mixtures of palladium acetate and triphenylphosphine or tri-(ortho-tolyl)-phosphine. The reaction can also be carried out by first forming a complex of the halide and the catalyst system and then reacting this with the olefin in the presence of a tertiary amine. On the other hand, it is known that the reaction of benzoyl chloride with methyl acrylate in the presence of stoichiometric amounts of a nickel(O) catalyst, followed by treatment of the reaction mixture with iodine in methanol, leads to the formation of trans-(methyl 3-benzoylacrylate). Methyl cinnamate is formed as a by-product. Reaction of a complex of benzoyl-palladium chloride and tri-phenylphosphine with methyl acrylate at 70°–85° C. in the presence of triethylamine gives methyl cinnamate as the main product and methyl benzoylacrylate as a by-product. If the palladium and triphenylphosphine are employed in only catalytic amounts, the reaction equilibrium shifts in favour of the formation of methyl benzoylacrylate (weight ratio of methyl benzoylacrylate: methyl cinnamate =about 8.3:1) [cf. Transition Met. Chem. 2, 270 (1977) and 4, 398 (1979)]. Finally, Synthesis, 777 (1977) discloses that the reaction of an aromatic acid halide with a 1-alkyne in the presence of a Pd catalyst leads, without decarbonylation, to alkynyl ketones.

It has now been found that compounds of the formula I

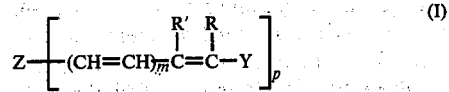

in which m is zero or 1, p is 1 or 2, Z is substituted or unsubstituted phenyl or naphthyl if p=1, and substituted or unsubstituted phenylene or naphthylene if p=2, R is hydrogen, $C_{1-4}$-alkyl, -CH$_2$COOR" or -CH$_2$CH$_2$CN and R' is hydrogen, or, if p=1 and m=zero, can also be $C_{1-4}$-alkyl, -CN or -COOR", but at least one of R and R' must be hydrogen, Y is —CN, —COOR", —CON(R")$_2$ or -COR" and the radicals R", independently of one another, are $C_1$-$C_{12}$-alkyl or phenyl, can be prepared by a process which comprises reacting a compound of the formula II

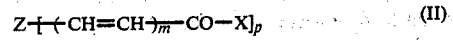

in which Z, m and p are as defined for formula I and X is chlorine, bromine or iodine, with a compound of the formula III or if desired, where p=2, with a mixture of two different compounds of the formula III

in which R, R' and Y are as defined for formula I, in the presence of a base and with the addition, as a catalyst, of palladium metal or of a palladium compound which under the reaction conditions forms a phosphorus-free labile palladium(O) compound.

Using the process according to the invention, the compounds of the formula I can be prepared in a simple economical manner from easily accessible starting materials. It is surprising that the reaction takes place selectively, with decarbonylation of the acid halide of the formula II.

The substituents present in a group Z are inert under the reaction conditions. The group Z can be monosubstituted or polysubstituted, and in the latter case the substituents can be identical or different.

Examples of substituents present on group Z are halogen atoms, formyl, —CH(OCH$_3$)$_2$, -CH(OC$_2$H$_5$)$_2$,

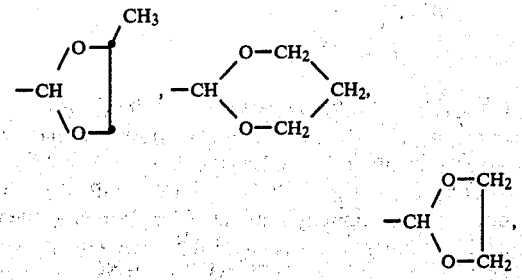

$C_{1-10}$-alkyl, $C_{1-16}$-alkoxy, phenoxy, di-($C_{1-10}$-alkyl)-amino, nitro, cyano, chloromethyl, trifluoromethyl, benzyl, $C_{1-4}$-alkylsulfonyl, —CO-$C_{1-10}$-alkyl, -CO-phenyl,

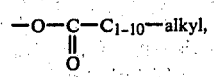

-COO-$C_{1-10}$-alkyl, -COO-phenyl, phenyl or naphthyl groups, which in turn can be substituted by halogen atoms or $C_{1-10}$-alkyl, $C_{1-10}$-alkoxy, di-($C_{1-10}$-alkyl)-amino, nitro, cyano, trifluoromethyl, —CO-$C_{1-10}$-alkyl, —CO-phenyl, -COO-$C_{1-10}$-alkyl or —COO-phenyl groups.

Phenyl and naphthyl substituents present on groups Z are preferably monosubstituted or unsubstituted. Alkyl groups R", and alkyl and alkoxy groups in the substituents mentioned above, can be straight-chain or branched and preferably have 1-8, and especially 1-4, C atoms. Examples of halogen substituents are fluorine, chlorine and bromine. Examples of groups R", as defined above, and of substituents present on groups Z are the methyl, ethyl, n-propyl, isopropyl, n-, sec.- and tert.-butyl, n-pentyl, 2-pentyl, n-hexyl, n-heptyl, n-octyl and n-decyl group; the methoxy, ethoxy, n-propoxy, n-butoxy, n-hexyloxy and n-decyloxy group; the N,N-dimethylamino, N,N-diethylamino, N,N-di-n-propylamino, N,N-di-n-butylamino, N,N-di-n-hexylamino, N,N-di-n-octylamino, N-methyl-N-ethylamino, N-methyl-N-n-propylamino, N-ethyl-N-n- hexylamino and N-ethyl-N-n-butylamino group; the methylsulfonyl and ethylsulfonyl group; the acetyl, propionyl, butyryl, valeroyl and octanoyl group; and the carboxylic acid methyl ester, ethyl ester, n-propyl ester, isopropyl ester, n-butyl ester, n-pentyl ester, n-hexyl ester, n-heptyl ester and n-decyl ester group.

Alkyl groups R and R' are preferably straight-chain and have one or two C atoms. X in formula II is preferably chlorine.

Compounds of the formula II are in particular:

1. Compounds of the formula IIa

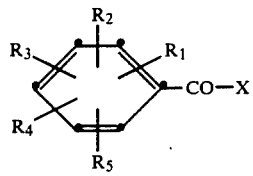

in which X is chlorine or bromine, $R_1$ is hydrogen, Cl, Br, F, formyl, $-CH(OCH_3)_2$, $-CH(OC_2H_5)_2$,

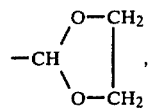

$C_{1-4}$-alkyl, $C_{1-4}$-alkoxy, phenoxy, di-$(C_{1-2}$-alkyl)-amino, $-NO_2$, $-CN$, $-CF_3$, $-CH_2Cl$, $C_{1-4}$-alkylsulfonyl, benzyl, $-CO-C_{1-4}$-alkyl, $-CO$-phenyl, $-OCO-C_{1-4}$-alkyl, $-COO-C_{1-4}$-alkyl, $-COO$-phenyl, phenyl, chlorophenyl, bromophenyl, methylphenyl, methoxyphenyl or 1- or 2-naphthyl, $R_2$ and $R_3$ independently of one another are hydrogen, Cl, Br, F, $-NO_2$, $C_{1-4}$-alkyl or $C_{1-4}$-alkoxy, especially methyl or methoxy and $R_4$ and $R_5$ are hydrogen or, if $R_1$, $R_2$ and $R_3$ are each chlorine, bromine, fluorine or methyl, can also be chlorine, bromine, fluorine or methyl. Preferred compounds of the formula IIa are those in which X is chlorine, $R_1$ is hydrogen, Cl, Br, F, I, chloromethyl, $C_{1-4}$-alkyl, especially methyl or ethyl, methoxy, $-OCOCH_3$, $-COOCH_3$, $-NO_2$, $-CN$, formyl, methylsulfonyl or phenyl, $R_2$ is hydrogen, Cl, Br, F, methyl, ethyl, methoxy or nitro, $R_3$ is hydrogen, Cl, Br, F, methyl, ethyl or methoxy and $R_4$ and $R_5$ are each hydrogen or, if $R_1$, $R_2$ and $R_3$ are Cl or F, can also be Cl or F.

2. Compounds of the formula IIb

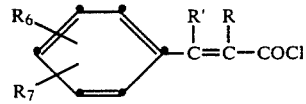

in which one of R and R' is hydrogen and the other is hydrogen or methyl, or R is hydrogen and R' is $-COO$-alkyl having 1–4 C atoms in the alkyl moiety, $R_6$ is hydrogen, Cl, Br, F, $-NO_2$, $-CN$, $-SO_2CH_3$, methyl, ethyl, methoxy, ethoxy, -CHO or $-CH(OCH_3)_2$ and $R_7$ is hydrogen, Cl, Br, F, $-NO_2$, methyl, ethyl, methoxy or ethoxy. Preferred compounds of the formula IIb are those in which $R_6$ is hydrogen, methyl, methoxy, Cl, Br, F, $-NO_2$ or $-CHO$, $R_7$ is hydrogen, one of R and R' is hydrogen and the other is hydrogen or methyl, or R is hydrogen and R' is $-COOCH_3$ or $-COOC_2H_5$.

3. Compounds of the formula IIc

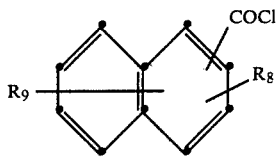

in which the $-COCl$ group is in the 1- or 2-position, $R_8$ and $R_9$ may be on the same ring or on different rings, $R_8$ is hydrogen, Cl, Br, F, methyl, ethyl, methoxy, ethoxy, $-CHO$, $-COCH_3$, $-SO_2CH_3$, $-CN$, $-NO_2$ or $-CH(OCH_3)_2$ and $R_9$ is hydrogen, Cl, Br, F, methyl, methoxy or $-NO_2$. Preferred compounds of the formula IIc are those in which $R_8$ is methyl and especially hydrogen and $R_9$ is hydrogen.

4. Compounds of the formula IId

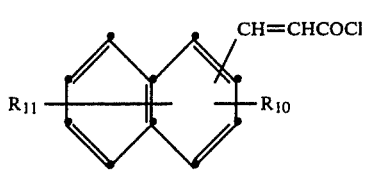

in which the group $-CH=CHCOCl$ is in the 1- or 2-position, $R_{10}$ and $R_{11}$ can be on the same ring or on different rings, $R_{10}$ is hydrogen, Cl, Br, F, methyl, methoxy, $-NO_2$, $-CHO$, $-CN$, $-SO_2CH_3$ or $-CH(OCH_3)_2$ and $R_{11}$ is hydrogen, Cl, Br, F, methyl, methoxy or $-NO_2$. Preferred compounds of the formula IId are those in which $R_{10}$ is methyl and especially hydrogen and $R_{11}$ is hydrogen.

5. Compounds of the formula IIe

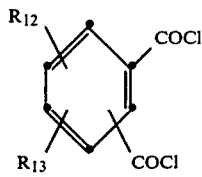

in which $R_{12}$ is hydrogen, $-CO$-phenyl, Cl, Br, F, $-CN$, $-CHO$, $-NO_2$ or methyl and $R_{13}$ is hydrogen, Cl, Br, F or methyl. Preferred compounds of the formula IIe are isophthalic acid dichloride and terephthalic acid dichloride, which can be substituted by a methyl or $NO_2$ group, though the unsubstituted compounds are particularly preferred.

6. Compounds of the formula IIf

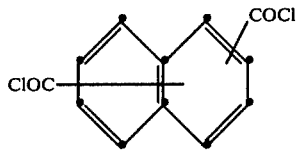

in which the $-COCl$ groups can be on the same ring or on different rings. Preferred compounds of the formula IIf are 1,4- and 2,6-naphthalenedicarboxylic acid dichloride.

7. Compounds of the formula IIg

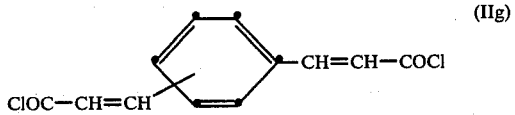

in which the —CH=CH—COCl groups are preferably in the 1,3- or 1,4-position.

8. Compounds of the formula IIh

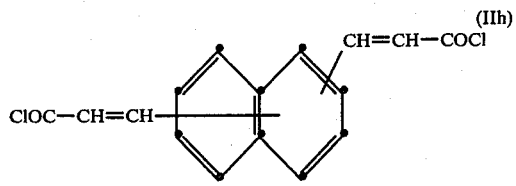

in which the -CH=CH-COCl groups are on the same ring or on different rings and are preferably in the 1,4- or 2,6-position.

Preferred meanings of R and R' are the following: R and R'=hydrogen, R=hydrogen and R'=methyl, —CN or -COOR" (p=1) or R'=hydrogen and R=methyl, —CH$_2$COOR" or —CH$_2$CH$_2$CN, R" being alkyl having 1-4, and especially 1 or 2, C atoms. Y is preferably —CN, —COR", —COOR" or —CON(R")$_2$ R" being alkyl having 1-4, and especially 1 or 2, C atoms.

Preferred compounds of the formula I, in which p=2, are symmetrical compounds, i.e. those in which R and Y in the two groups —CH=C(R)—Y or —CH=CH—CH=C(R)-Y (R'=H) have the same meaning.

Particularly preferred acid halides are compounds of the formula IIa, in which X is chlorine, one of R and R' is hydrogen and the other is hydrogen or methyl, or R is hydrogen and R' is -COOalkyl having 1-4 C atoms in the alkyl moiety, R$_1$ is hydrogen, Cl, Br, F, I, formyl, methyl, methoxy, chloromethyl, cyano, nitro, —OCOCH$_3$, —COOCH$_3$ or phenyl, R$_2$ is hydrogen, Cl, F, methyl or methoxy, R$_3$ is hydrogen, Cl, F or methoxy and R$_4$ and R$_5$ are each hydrogen, or, if R$_1$, R$_2$ and R$_3$ are Cl or F, can also be Cl or F; compounds of the formula IIb in which R$_6$ is hydrogen, chlorine or nitro and R$_7$ is hydrogen; and compounds of the formula IIc, in which the group —COCl is in the 1- or 2-position, R$_8$ is methyl or, especially, hydrogen, and R$_9$ is hydrogen, isophthalic acid dichloride, terephthalic acid dichloride and 1,4- or 2,6-naphthalenedicarboxylic acid dichloride. The most preferred compounds are 4-formylbenzoyl chloride, 4-bromobenzoyl chloride and especially benzoyl chloride.

Preferred compounds of the formula III are those in which R and R' are hydrogen and Y is —CN, —COR", —COOR" or —CON(R")$_2$, R" being methyl or ethyl; R is hydrogen, R' is methyl and Y is —CN, —COOCH$_3$, —COOC$_2$H$_5$, —CON(CH$_3$)$_2$ or —CON(C$_2$H$_5$)$_2$; R is hydrogen and R' and Y are each —CN, —COOCH$_3$ or —COOC$_2$H$_5$, R' is hydrogen, R is methyl and Y is —CN, —COOCH$_3$, —COOC$_2$H$_5$, —CON(CH$_3$)$_2$ or —CON(C$_2$H$_5$)$_2$; R' is hydrogen, R is —CH$_2$COOCH$_3$ and Y is —COOCH$_3$; or R' is hydrogen, R is —CH$_2$CH$_2$CN and Y is -CN. The most preferred compounds of the formula III are ethyl acrylate, acrylonitrile and N,N-diethylacrylamide.

The catalysts, and the compounds of the formulae II and III are known or can be prepared by methods known per se. For the preparation of the compounds of the formula II, cf., for example, Organikum, 387–388, VEB Deutscher Verlag der Wissenschaften, Berlin 1964, and Survey of Organic Syntheses, Wiley Interscience (1970), pages 860–873.

The compounds of the formulae II and III are employed in not less than the stoichiometric amount. Preferably, an excess of the compounds of the formula III is employed, for example up to about 1.5 mol of this compound per acid halide group.

In addition to palladium metal itself, palladium compounds as defined are, for example, compounds of the formula IV $$M^y[PdL_n]^x \qquad (IV)$$

in which n is an integer from 2 to 4, x=2$^+$ to 2$^-$, y=—(x), M, if x is not 0, is a counter-ion, and the L's are identical or different phosphorus-free ligands, for example Cl, Br, I, —CN, —NO$_3$, —C$_{1-12}$-alkyl-COO,

NH$_3$, 2,2'-bipyridyl, o-phenanthroline,

and -NC-phenyl. Examples of suitable compounds of the formula IV are PdCl$_2$, PdBr$_2$, Pd(CN)$_2$, Pd(NO$_3$)$_2$ and Pd(O$_2$C—C$_{1-12}$-alkyl)$_2$, and especially Pd(OOCCH$_3$)$_2$,

[Pd(NH$_3$)$_4$]Cl$_2$, [PdCl$_4$]Na$_2$, Pd(OOCCH$_3$)$_2$(2,2'-bipyridyl), Pd(OOCCH$_3$)$_2$(o-phenanthroline),

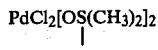

and PdCl$_2$(NC-phenyl)$_2$.

In addition to the above compounds, compounds of palladium in other oxidation levels can also be employed, for example bis-(dibenzylidene-acetone)-palladium(O) and bis-(isonitrile)-palladium(O) compounds. Examples of the latter category are bis-(cyclohexylisonitrile)-palladium(O), bis-(isopropylisonitrile)-palladium(O), bis-(tert.-butylisonitrile)-palladium(O), bis-(p-tolylisonitrile)-palladium(O), bis-(phenylisonitrile)-palladium(O) and bis-(p-methoxyphenylisonitrile)-palladium(O). Amongst the above compounds, bis-(dibenzylidene-acetone)-palladium(O), bis-(cyclohexylisonitrile)-palladium(O) and bis-(isopropylisonitrile)-palladium(O) are preferred.

Preferred catalysts are PdCl$_2$, PdBr$_2$, Pd(OOCCH$_3$)$_2$,

Pd(OOCCH$_3$)$_2$(2,2'-bipyridyl), PdCl$_2$(NC-phenyl)$_2$, bis-(dibenzylidene-acetone)-palladium(O) and bis-(cyclohexylisonitrile)-palladium(O). The most preferred are PdCl$_2$, palladium acetate and bis-(dibenzylideneacetone)-palladium(O).

The catalysts are in general employed in an amount of 0.0001 to 20 mol %, preferably 0.001 to 3 mol %, based on the compound of the formula II.

Bases used in the process according to the invention can be inorganic or organic compounds, which are adequately soluble in the reaction medium. Examples are compounds of the formulae V to VII

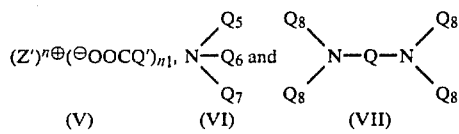

(V)   (VI)   (VII)

and cyclic tertiary amines, for example N-methylpiperidine, N-ethylpiperidine, 1,2,2,6,6-pentamethylpiperidine, 4-oxo-1,2,2,6,6-pentamethylpiperidine, 1,4-diazabicyclo[2.2.2]octane (DABCO), N-alkylmorpholines and N-alkylpyrrolidines, such as N-methylmorpholine, N-ethylmorpholine, N-methylpyrrolidine and N-ethylpyrrolidine, and N,N'-dialkylpiperazines, such as N,N'-dimethylpiperazine.

In the above formulae $n_1$ is 1 or 2, Q' is phenyl or $C_{1-17}$-alkyl, Z' is an alkali metal cation, an alkaline earth metal cation or

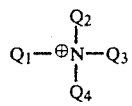

Q is straight-chain or branched alkylene having 2–6 C atoms, $Q_1$ is hydrogen, $C_{1-12}$-alkyl, cyclopentyl, cyclohexyl, benzyl or phenyl, $Q_2$, $Q_3$ and $Q_4$ are identical or different $C_{1-12}$-alkyl, $Q_5$ is $C_{1-12}$-alkyl, cyclopentyl, cyclohexyl, phenyl or benzyl, which can also be substituted, for example by a halogen atom, such as chlorine or bromine, or by an alkyl or alkoxy group, each having 1–4, and especially 1 or 2, C atoms, $Q_6$ and $Q_7$ are identical or different $C_{1-12}$-alkyl and $Q_8$ is methyl or ethyl.

An alkali metal cation Z' is, in particular, the sodium cation and especially the lithium cation. Alkyl groups Q' and $Q_1$ to $Q_7$ can be straight-chain or branched. Where $Q_5$ and $Q_7$ are alkyl groups, these can advantageously conjointly have not less than 9 C atoms, whilst alkyl groups $Q_1$ to $Q_4$ preferably each have 1–4 C atoms.

Examples of compounds of the formulae V to VII are lithium acetate, lithium butyrate, lithium stearate, barium acetate, calcium acetate, potassium stearate, calcium stearate, sodium stearate, lithium benzoate, sodium benzoate and the corresponding trimethylammonium, tetramethylammonium, tetraethylammonium and tetra-n-butylammonium salts; triethylamine, tri-n-butylamine, tri-(2-ethylhexylamine), tri-n-octylamine and tri-n-dodecylamine; N-benzyl-dialkylamines, such as N-benzyldimethylamine, N-benzyldiethylamine, N-(4-chlorobenzyl)-dimethylamine and N-(3-methylbenzyl or 3-methoxybenzyl)-dimethylamine; N,N,N',N'-tetramethyl-ethylenediamine, N,N,N',N'-tetraethylethylenediamine, N,N,N',N'-tetramethyl-1,3-diaminopropane and N,N,N',N'-tetramethyl-1,6-diaminohexane.

Preferred bases are tertiary amines of the above type, especially N-ethylmorpholine, or compounds of the formula VI, in which $Q_5$ is 4-chlorobenzyl, 3-methylbenzyl, 3-methoxybenzyl or especially benzyl, and $Q_6$ and $Q_7$ are each alkyl having 1–4 C atoms, especially 1 or 2 C atoms, or wherein $Q_5$, $Q_6$ and $Q_7$ are each alkyl having 3–12 C atoms. N-Benzyldimethylamine, N-ethylmorpholine and tri-n-butylamine are especially preferred.

The reaction according to the invention is advantageously carried out at a temperature between 0° and 200° C., preferably between 90° and 150° C. If the acid halide of the formula II is liquid, the reaction can be carried out without adding a solvent. Preferably, however, the reaction is carried out in an organic solvent which is inert towards the reactants. Examples of suitable inert organic solvents are aliphatic, cycloaliphatic or aromatic hydrocarbons and chlorohydrocarbons, such as n-pentane, n-heptane, n-octane, cyclopentane, cyclohexane, benzene, toluene, xylenes and chlorobenzene; aromatic, aliphatic and cyclic ethers, such as anisole, diethyl ether, diisopropyl ether, tetrahydrofuran and dioxane; nitriles, especially benzonitrile and alkylnitriles having 2–5 C atoms, such as acetonitrile, propionitrile and butyronitrile; 3-methoxypropionitrile and 3-ethoxypropionitrile; N,N-dialkylamides of aliphatic monocarboxylic acids, having 1–3 C atoms in the acid moiety, such as N,N-dimethylformamide, N,N-dimethylacetamide and N,N-diethylacetamide; tertiary alcohols having 4–8 C atoms, especially tert.-butanol; aliphatic and cycloaliphatic ketones, such as acetone, diethyl ketone, methyl isopropyl ketone, cyclopentanone and cyclohexanone; esters, such as esters of carbonic acid, for example diethyl carbonate, and alkyl esters or alkoxyalkyl esters of aliphatic monocarboxylic acids, having a total of 2-8 C atoms, such as methyl acetate, ethyl acetate, n-butyl acetate, isobutyl acetate, ethyl butyrate, n-butyl butyrate and 1-acetoxy-2-methoxyethane. Preferred solvents are nitriles, ketones, esters, cyclic ethers and aromatic hydrocarbons of the above type.

Especially suitable solvents for the reaction in the presence of an inorganic base are polar solvents, such as nitriles, ketones and esters. The most preferred method of carrying out the reaction is in the presence of an organic base and of an aromatic ether or hydrocarbon, especially anisole, a xylene or toluene.

In the process according to the invention, the course of the reaction can easily be followed from the evolution of CO, for example by means of a bubbler. In the case of reaction products of limited solubility in the reaction mixture, it is advisable to stop the reaction when the evolution of CO has ceased, and to work up the reaction product directly.

Many of the compounds of the formula I, obtainable according to the invention, and their uses are known; for example, the compounds can be used in a manner known per se, with or without prior conversion to derivatives having suitable functional groups, such as —COOH, —COCl or carboxylic acid ester groups, for the preparation of photocrosslinkable polymers, by reacting them with polymers having suitable functional groups, for example polymers having NH$_2$ or OH groups, such as poly-(aminostyrene), polyvinyl alcohol or cellulose. Compounds of the formula I, in which p is 2, can also be condensed with suitable co-components, especially diols or diamines, to give photocrosslinkable polymers. Such polymers are used, for example, as (socalled) photoresists, or for other photographic purposes, such as copying materials, printing plates and the like [cf., for example, U.S. Pat. Nos. 2,670,285, 3,148,064, 3,218,168, 3,307,941, 3,387,967, 3,748,131 and 3,929,489].

Further uses of cinnamic acids, cinnamic acid esters and cinnamonitriles are described, for example, in Chemical Abstracts, 78, 12699; 80, 4394, 15756 and 29709; 82, 17887 and 103009; inter alia, these uses include adhesive additives, crosslinking agents for polymers, stabilisers for insecticides, scents and rustproofing agents.

Compounds

in which R and R' are hydrogen or $C_{1-4}$-alkyl, but one of R and R' must be hydrogen, and Y is as defined for formula I, and in which the benzene ring can also be substituted further, for example by alkyl, nitrile or alkylsulfonyl groups, are also valuable intermediates for the preparation of optical brighteners (cf., for example, British Patent Specification No. 1,536,480).

EXAMPLE 1

Ethyl Cinnamate 3.51 g (0.025 mol) of benzoyl chloride, 3.125 g (0.03125 mol) of ethyl acrylate, 5.79 g (0.03125 mol) of tri-n-butylamine, 50 ml of toluene and 0.0561 g (0.00025 mol) of palladium acetate are introduced into a 100 ml glass flask and heated to 100° C., with stirring. A slight evolution of gas is observed. After the mixture has been stirred for 4 hours, it is cooled and the contents of the flask are extracted by shaking twice with 25 ml of 2 N hydrochloric acid at a time. The toluene phase is dried with magnesium sulfate and distilled. After the toluene has been distilled off, 2.9 g (0.0165 mol) of ethyl cinnamate are obtained, corresponding to a yield of 66% of theory; boiling point = 135°–138° C./17×10² Pa; $n_D^{20} = 1.5592$.

Examples 2–9

The procedure described in Example 1 is repeated, except that (a) 50 ml of dioxane, (b) 50 ml of ethyl butyrate, (c) 50 ml of propionitrile, (d) 50 ml of diethyl carbonate, (e) 50 ml of chlorobenzene, (f) 50 ml of cyclohexane, (g) 50 ml of tert.-butanol or (h) 50 ml of N,N-dimethylformamide are used in place of 50 ml of toluene. After working up as described in Example 1, ethyl cinnamate is obtained in comparably good yields.

EXAMPLES 10–18

The procedure described in Example 1 is repeated, except that 0.03125 mol of one of the bases tri-n-octylamine, tris-(2-ethylhexyl)-amine, ethyl-dicyclohexylamine, triethylamine, ethyl-diisopropylamine, N-methyl-2,2,6,6-tetramethylpiperidine, lithium acetate and trimethyl-benzylammonium acetate is used in place of 0.03125 mol of tri-n-butylamine. After working up as described in Example 1, ethyl cinnamate is obtained in comparably good yields.

EXAMPLES 19–24

The procedure described in Example 1 is repeated, except that 0.00025 mol of one of the palladium compounds bis-(dibenzylidene-acetone)-palladium (O), palladium nitrate .2H₂O, bis-(acetylacetonato)-palladium-(II), palladium chloride and palladium cyanide is used in place of 0.00025 mol of palladium acetate. After working up as described in Example 1, ethyl cinnamate is obtained in yields of 73–82% of theory.

EXAMPLE 25 tert.-Butyl cinnamate

The procedure described in Example 1 is repeated, except that 4 g (0.03125 mol) of tert.-butyl acrylate are used in place of 3.125 g (0.03125 mol) of ethyl acrylate. After a reaction time of 15 minutes at 133° C., 2.28 g (0.0179 mol) of tert.-butyl cinnamate are obtained, corresponding to a yield of 57% of theory; boiling point = 144° C./10×10² Pa.

EXAMPLE 26

The procedure described in Example 1 is repeated, except that 0.0112 g (0.00005 mol) of palladium acetate is used in place of 0.0561 g (0.00025 mol) of palladium acetate. After a reaction time of 6 hours at 120° C., ethyl cinnamate is obtained in a yield of 69% of theory.

EXAMPLE 27

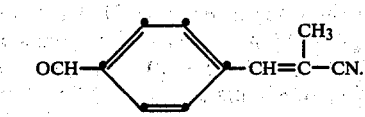

The procedure described in Example 1 is repeated, except that 3.49 g (0.025 mol) of p-formylbenzoyl chloride and 2.09 g (0.03125 mol) of methacrylonitrile are used. After a reaction time of 2 hours at 120° C., in 50 ml of p-xylene as the solvent, 1.35 g (0.0079 mol) of the above compound, corresponding to a yield of 31.6% of theory, are obtained as a 60:40 Z/E mixture; melting point = 63.64° C. Analysis for $C_{11}H_9NO$ (molecular weight 171): calculated C 77.17% H, 5.30%, N 8.18%; found C 77.11%, H 5.36%, N 8.16%.

Example 28

Cinnamonitrile

The procedure described in Example 1 is repeated, except that 3.31 g (0.0625 mol) of acrylonitrile, 7.02 g (0.05 mol) of benzoyl chloride, 11.6 g (0.0625 mol) of tri-n-butylamine, 100 ml of p-xylene and 0.1122 g (0.0005 mol) of palladium acetate are used. After a reaction time of 2 hours at 120° C., 3.47 g (0.27 mol) of cinnamonitrile are obtained, corresponding to a yield of 54% of theory. Boiling point = 134°–136° C./17×10² Pa.

EXAMPLE 29

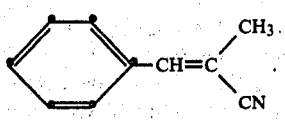

The procedure described in Example 28 is repeated, except that 4.2 g (0.0625 mol) of methacrylonitrile are used in place of 3.31 g (0.0625 mol) of acrylonitrile. After a reaction time of 3 hours at 120° C., 3.19 g (0.0224 mol) of the above compound, corresponding to a yield of 44.8% of theory, are obtained as a 50:50 E/Z mixture; boiling point=120° C./19×10² Pa.

EXAMPLE 30

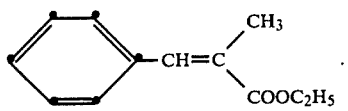

The procedure described in Example 28 is repeated, except that 7.1 g (0.0625 mol) of ethyl methacrylate are used in place of 3.31 g (0.062 mol) of acrylonitrile. After a reaction time of 3 hours at 120° C., 2.7 g (0.0142 mol) of the above compound, corresponding to a yield of 28.4% of theory, are obtained as the pure E-isomer; boiling point=155°-160° C./40×10² Pa.

EXAMPLE 31

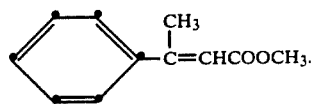

The procedure described in Example 28 is repeated, except that 6.25 g (0.0625 mol) of methyl crotonate are used in place of 3.31 g (0.0625 mol) of acrylonitrile. After a reaction time of 6 hours at 120° C., 2.9 g (0.0165 mol) of the above compound, corresponding to a yield of 33% of theory, are obtained in the form of white crystals (consisting only of E-isomer); melting point×40° C. Analysis for $C_{11}H_{12}O_2$ (molecular weight 176): calculated C 74.95%, H 6.78%; found C 74.93%, H 6.9%.

EXAMPLE 32

Cinnamic acid N,N-diethylamide

The procedure described in Example 28 is repeated, except that 7.9 g (0.0625 mol) of acrylic acid N,N-diethylamide are used in place of 3.31 g (0.0625 mol) of acrylonitrile. After a reaction time of 2 hours at 120° C., 7.1 g (0.035 mol) of cinnamic acid N,N-diethylamide, corresponding to a yield of 70% of theory, are obtained in the form of white crystals; melting point=65° C. Analysis for $C_{13}H_{17}NO$ (moleculare weight 203): calculated C 76.81%, H 8.43%, N 6.89%; found C 76.63%, H 8.70%, N 6.89%.

EXAMPLE 33

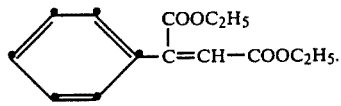

The procedure described in Example 28 is repeated, except that 10.7 g (0.0625 mol) of diethyl maleate are used in place of 3.31 g (0.0625 mol) of acrylonitrile. After a reaction time of 4 hours at 120° C., 5.5 g (0.222 mol) of ethyl phenylmaleate, corresponding to a yield of 44.4% of theory, are obtained as a colourless liquid (consisting only of E-isomer); boiling point 123°-124° C./106 Pa. Analysis for $C_{14}H_{16}O_4$ (molecular weight 248): calculated C 67.73%, H 6.50%; found C 68.03%, H 6.72%.

EXAMPLE 34

The procedure described in Example 1 is repeated, except that 4.62 g (0.025 mol) of benzoyl bromide are used in place of 3.51 g (0.025 mol) of benzoyl chloride. After a reaction time of 5 hours at 120° C., 0.7 g (0.004 mol) of ethyl cinnamate are obtained, corresponding to a yield of 18% of theory.

EXAMPLE 35

The procedure described in Example 1 is repeated, except that 5.8 g (0.025 mol) of benzoyl iodide are used in place of 3.51 g (0.025 mol) of benzoyl chloride. After a reaction time of 4 hours at 120° C., 2.78 g (0.158 mol) of ethyl cinnamate are obtained, corresponding to a yield of 63% of theory.

EXAMPLE 36

Ethyl 4-bromocinnamate

The procedure described in Example 1 is repeated, except that 5.49 g (0.025 mol) of 4-bromobenzoyl chloride are used in place of 3.51 g (0.025 mol) of benzoyl chloride. After a reaction time of 1 hour at 120° C. in 50 ml of p-xylene as the solvent, 3.8 g (0.0149 mol) of ethyl 4-bromocinnamate, corresponding to a yield of 60% of theory, are obtained as a colourless liquid; boiling point 180° C./21×10² Pa.

EXAMPLE 37

Ethyl 4-chlorocinnamate

The procedure described in Example 28 is repeated, except that 8.75 g (0.05 mol) of 4-chlorobenzoyl chloride are used in place of 7.02 g (0.05 mol) of benzoyl chloride. After working up, 8.3 g (0.0394 mol) of ethyl 4-chlorocinnamate, corresponding to a yield of 79% of theory, are obtained as a colourless liquid; boiling point 108° C./106 Pa. Analysis for $C_{11}H_{11}O_2Cl$ (molecular weight 210.5): calculated C 62.72%, H 5.26%; found C 62.69%, H 5.38%.

EXAMPLE 38

The procedure described in Example 1 is repeated, except that 2.54 g (0.0125 mol) of terephthalic acid dichloride are used in place of 3.51 g (0.025 mol) of benzoyl chloride. After a reaction time of 5.5 hours at 110° C., 0.15 g (0.00055 mol) of diethyl phenylene-4,4'-bis-acrylate are obtained, corresponding to a yield of 4.4% of theory; melting point 93°-96° C.

EXAMPLE 39

Ethyl 4-formylcinnamate

The procedure described in Example 28 is repeated, except that 8.23 g (0.05 mol) of 4-formylbenzoyl chloride and 6.25 g (0.0625 mol) of ethyl acrylate are used. After a reaction time of 13 hours at 120° C., 4.7 g (0.023 mol) of ethyl 4-formylcinnamate are obtained, corresponding to a yield of 46% of theory; boiling point 137°-140° C./13 Pa.

EXAMPLE 40

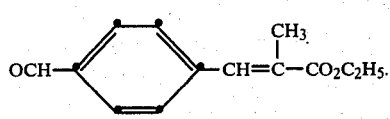

The procedure described in Example 28 is repeated, except that 8.23 g (0.05 mol) of p-formylbenzoyl chloride and 7.13 g (0.0625 mol) of ethyl methacrylate are used. After a reaction time of 2 hours at 120° C., 3.2 g (0.0147 mol) of ethyl p-formyl-α-methylcinnamate are obtained, corresponding to a yield of 29.4% of theory; boiling point 127°–131° C./7 Pa.

EXAMPLE 41

4-Formylcinnamonitrile

The procedure described in Example 28 is repeated, except that 8.23 g (0.05 mol) of 4-formylbenzoyl chloride and 3.32 g (0.0625 mol) of acrylonitrile are used. After a reaction time of 3 hours at 120° C., 3.5 g (0.0223 mol) of 4-formylcinnamonitrile are obtained, corresponding to a yield of 44.6% of theory; melting point 122° C. Analysis for $C_{10}H_7NO$ (molecular weight 157): calculated C 76.22%, H 4.49%, N 8.91%, found C 76.30%, H 4.55%, N 8.96%.

EXAMPLE 42

3-Methoxycinnamonitrile

The procedure described in Example 1 is repeated, except that 17.05 g (0.1 mol) of 3-methoxybenzoyl chloride, 6.63 g (0.125 mol) of acrylonitrile, 12.96 g (0.1 mol) of ethyldiisopropylamine, 0.1773 g (0.001 mol) of palladium chloride and 50 ml of cyclohexanone, as the solvent, are used. After a reaction time of 13 hours at 120° C, 1 g (0.0063 mol) of 3-methoxycinnamonitrile are obtained, corresponding to a yield of 6.3% of theory; boiling point 159°–166° C./19×10² Pa.

EXAMPLE 43

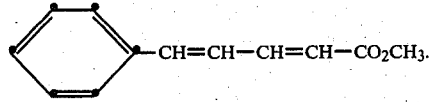

The procedure described in Example 28 is repeated, except that 8.35 g (0.05 mol) of cinnamyl chloride and 5.4 g (0.0625 mol) of methyl acrylate are used. After a reaction time of 50 hours at 120° C., 6.10 g (0.0325 mol) of methyl 5-phenyl-2.4-pentadienecarboxylate are obtained, corresponding to a yield of 65% of theory; melting point 71° C.

EXAMPLE 44

Ethyl β-(2-naphthyl)-acrylate

The procedure described in Example 28 is repeated, except that 9.55 g (0.05 mol) of 2-naphthoyl chloride and 6.25 g (0.0625 mol) of ethyl acrylate are used. After a reaction time of 2 hours at 120° C., 9.9 g (0.044 mol) of ethyl β-(2-naphthyl)-acrylate are obtained, corresponding to a yield of 88% of theory; boiling point 106°–110° C./4 Pa. Analysis for $C_{15}H_{14}O_2$ (molecular weight 188): calculated C 79.62%, H 6.24%, O 14.14%; found C 79.39%, H 6.49%, O 14.08%.

EXAMPLE 45

4-Fluorocinnamonitrile

The procedure described in Example 1 is repeated, except that 15.86 g (0.1 mol) of 4-fluorobenzoyl chloride, 26.95 g (0.1 mol) of tri-n-hexylamine, 6.53 g (0.125 mol) of acrylonitrile and 0.575 g (0.001 mol) of bis-(dibenzylidene-acetone)-palladium(O) in 50 ml of dioxane are used. After a reaction time of 33 hours at 100° C., 2.63 g (0.0179 mol) of 4-fluorocinnamonitrile are obtained, corresponding to a yield of 17.9% of theory; analysis for $C_9H_6FN$ (molecular weight 147): calculated C 73.46%, H 4.11%, N 9.52%; found C 73.16%, H 4.19%, N 9.61%.

EXAMPLE 46

3-Bromocinnamonitrile

The procedure described in Example 1 is repeated, except that 21.94 g (0.1 mol) of 3-bromobenzoyl chloride, 6.63 g (0.125 mol) of acrylonitrile, 35.37 g (0.1 mol) of tris-(2-ethylhexyl)-amine and 0.3046 g (0.001 mol) of bis-acetylacetonato)-palladium(II) in 50 ml of propionitrile are used. After a reaction time of 3 hours at 100° C., 2.05 g (0.0099 mol) of 3-bromocinnamonitrile are obtained, corresponding to a yield of 9.9% of theory; melting point 62° C. Analysis for $C_9H_6NBr$ (molecular weight 208): calculated C 51.96%, H 2.91%, N 6.73%; found C 52.29%, H 2.95%, N 6.91%.

EXAMPLE 47

Ethyl 4-nitrocinnamate

The procedure described in Example 1 is repeated, except that 9.28 g (0.05 mol) of 4-nitrobenzoyl chloride, 6.25 g (0.0625 mol) of ethyl acrylate, 8.65 g (0.05 mol) of tri-n-butylamine and 0.1122 g (0.0005 mol) of palladium acetate are used. After a reaction time of 1 hour at 120° C. in 100 ml of p-xylene as the solvent, 6.1 g (0.0276 mol) of ethyl 4-nitrocinnamate are obtained, corresponding to a yield of 55.2% of theory; melting point 137.5° C. Analysis for $C_{11}H_{11}NO_4$ (molecular weight 221: calculated C 59.73%, H 5.01%, N 6.33%; found C 59.47%, H 4.96%, N 6.27%.

EXAMPLE 48

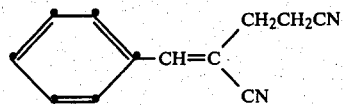

0.1122 g (5×10⁻⁴ mol) of palladium acetate, 5.77 ml (50 millimols) of benzoyl chloride, 6.75 ml (62.5 millimols) of 2-methyleneglutarodinitrile and 11.91 ml (50 millimols) of tri-n-butylamine in 100 ml of p-xylene are stirred for 3 hours at 120° C. The mixture is extracted by shaking with 100 ml of 2 N HCl, 50 ml of 2 N NaOH and 50 ml of water and is then dried for 15 minutes with 5 g of magnesium sulfate. The crude product is distilled in vacuo. 4.18 g (46% of theory) of the above compound are obtained as a colourless liquid. Analysis for $C_{12}H_{10}N_2$: calculated C 79.10%, H 5.53%, N 15.38%; found C 78.90%, H 5.87%, N 15.38%.

The following compounds are prepared analogously to the procedure described in Example 48

EXAMPLE 49

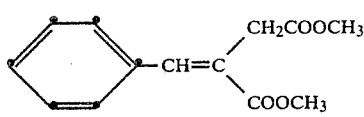

This compound is prepared from 7.9 g (50 millimols) of dimethyl itaconate and 6.76 g (50 millimols) of N-benzyldimethylamine; the reaction mixture is stirred for 1.5 hours at 130° C. The crude product is distilled at 105°–106° C./6.7 Pa. Yield 8.43 g (72% of theory), as a pale yellow liquid.

EXAMPLE 50

Br—⟨phenyl⟩—C(CN)=CH—CN.

This compound is prepared from 10.97 g (50 millimols) of 4-bromobenzoyl chloride, 4.88 g (62.5 millimols) of fumarodinitrile and 50 ml of o-xylene; the reaction mixture is stirred for 5 hours at 120° C. The crude product is chromatographed on silica gel in toluene and is then recrystallised from methanol. Yield 1.58 g (14% of theory) of pale brown crystals of melting point 185.3° C. Analysis for $C_{10}H_5BrN_2$: calculated C 51.54%, H 2.16%, N 12.02%; found C 51.51%, H 2.20%, N 11.98%.

EXAMPLE 51

⟨phenyl⟩—CH=CH—C(=O)—C₂H₅ (trans).

This compound is prepared from 4.2 g (50 millimols) of ethyl vinyl ketone and 6.76 g (50 millimols) of N-benzyldimethylamine; the reaction mixture is stirred for 2 hours at 130° C. The crude product is distilled in vacuo through a Vigreux column and is then recrystallised from n-pentane. Yield 3.81 g (48% of theory); melting point 35.5° C.; colourless crystals. Analysis for $C_{11}H_{12}O$: calculated C 82.46%, H 7.55%, O 9.99%; found C 82.25%, H 7.53%, O 10.30%.

EXAMPLE 52

Ethyl 4-methylcinnamate (trans)

0.1122 g ($5 \times 10^{-4}$ mols) of palladium acetate, 6.61 ml (50 millimols) of p-tolyl chloride, 6.78 ml (62.5 millimols) of ethyl acrylate and 11.91 ml (50 millimols) of tri-n-butylamine in 100 ml of p-xylene are stirred for 3 hours at 120° C. The mixture is extracted by shaking with 50 ml of 2 N HCl, 25 ml of 2 N NaOH and 25 ml of water, and is then dried for 15 minutes with 5 g of magnesium sulphate. The crude product is distilled in vacuo. 6.08 g (64% of theory) are obtained as a colourless liquid. Analysis for $C_{12}H_{14}O_2$: calculated C 75.77%, H 7.52%; found C 75.73%, H 7.54%.

The following compounds are prepared analogously to the procedure described in Example 52

EXAMPLE 53

Ethyl 4-cyanocinnamate (trans)

This compound is prepared from 8.28 g (50 millimols) of 4-cyanobenzoyl chloride; the reaction mixture is stirred for 2 hours at 120° C. The crude product is recrystallised once from cyclohexane and once from n-hexane. 8.79 g (88% of theory) of white crystals are obtained; melting point 71° C. Analysis for $C_{12}H_{11}NO_2$: calculated C 71.63%, H 5.5%, N 6.96%; found C 71.25%, H 5.38%, N 6.87%.

EXAMPLE 54

Ethyl 4-chloromethylcinnamate (trans)

This compound is prepared from 9.45 g (50 millimols) of 4-chloromethylbenzoyl chloride; the reaction mixture is stirred for 1¼ hours at 120° C. The crude product is chromatographed on silica gel in methylene chloride, and is then distilled. 4.5 g (40% of theory) of a colourless liquid are obtained. Analysis for $C_{12}H_{13}O_2Cl$: calculated C 64.15%, H 5.83%, O 14.24%, Cl 15.78%; found C 64.05%, H 5.87%, O 14.11%, Cl 15.63%.

EXAMPLE 55

Ethyl 3-methylcinnamate (trans)

This compound is prepared from 7.33 ml (50 millimols) of m-toluyl chloride; the reaction mixture is stirred for 2 hours at 120° C. The crude product is distilled in vacuo. 6.85 g (72% of theory) of a colourless liquid are obtained. Analysis for $C_{12}H_{14}O_2$: calculated C 75.77%, H 7.42%, O 16.82%; found C 75.61%, H 7.72%, O 17.06%.

EXAMPLE 56

Ethyl 2-chlorocinnamate (trans)

This compound is prepared from 6.37 ml (50 millimols) of 2-chlorobenzoyl chloride; the reaction mixture is stirred for 1.5 hours at 120° C. The crude product is distilled in vacuo. 7.8 g (74% of theory) of a colourless liquid are obtained. Analysis for $C_{11}H_{11}O_2Cl$: calculated C 62.77%, H 5.26%, O 15.19%, Cl 16.83%; found C 62.52%, H 5.36%, O 15.39%, Cl 16.67%.

EXAMPLE 57

Ethyl 2-methylcinnamate (trans)

This compound is prepared from 6.59 ml (50 millimols) of o-toluoyl chloride; the reaction mixture is stirred for 1.5 hours at 120° C. The crude product is distilled in vacuo. 7.37 g (78% of theory) of a colourless liquid are obtained. Analysis for $C_{12}H_{14}O_2$: calculated C 75.77%, H 7.42%, O 16.82%; found C 75.60%, H 7.65%, O 16.92%.

EXAMPLE 58

Ethyl 3-chlorocinnamate (trans)

This compound is prepared from 6.42 ml (50 millimols) of 3-chlorobenzoyl chloride; the reaction mixture is stirred for 2 hours at 120° C. The crude product is distilled in vacuo. 7.87 g (75% of theory) of a colourless liquid are obtained. Analysis for $C_{11}H_{11}O_2Cl$: calculated C 62.68%, H 5.27%, O 15.19%, Cl 16.86%; found C 62.63%, H 5.29%, O 15.27%, Cl 17.34%.

EXAMPLE 59

Ethyl 3-iodocinnamate (trans)

This compound is prepared from 13.33 g (50 millimols) of 3-iodobenzoyl chloride; the reaction mixture is stirred for 65 minutes at 120° C. The crude product is distilled in vacuo and is then recrystallised from methanol/water. 4.7 g (31% of theory) of white crystals are obtained; melting point 36.3° C. Analysis for $C_{11}H_{11}O_2I$: calculated C 43.71%, H 3.68%, O 10.60%, I 42.02%; found C 44.07%, H 3.61%, O 10.63%, I 41.25%.

EXAMPLE 60

Ethyl 2-acetoxycinnamate (trans)

This compound is prepared from 9.93 g (50 millimols) of 2-acetylsalicylyl chloride; the reaction mixture is stirred for 50 minutes at 120° C. The crude product is distilled in vacuo. 6.66 g (57% of theory) of a colourless liquid are obtained. Analysis for $C_{13}H_{14}O_4$: calculated C 66.66%, H 6.03%, O 27.23%; found C 66.18%, H 6.30%, O 27.06%.

EXAMPLE 61

Ethyl 4-phenylcinnamate (trans)

This compound is prepared from 10.83 g (50 millimols) of biphenyl-4-carboxylic acid chloride; the reaction mixture is stirred for 1.5 hours at 120° C. The crude product is chromatographed on silica gel in methylene chloride and recrystallised from n-hexane. 8.03 g (64% of theory) of white crystals are obtained; melting point 88.6° C. Analysis for $C_{17}H_{16}O_2$: calculted C 80.93%, H 6.39%, O 12.68%; found C 80.77%, H 6.28%, O 12.89%.

EXAMPLE 62

Ethyl 4-methoxycarbonylcinnamate (trans)

This compound is prepared from 9.93 g (50 millimols) of terephthalic acid chloride monomethyl ester; the reaction mixture is stirred for 1.5 hours at 120° C. The crude product is distilled in vacuo. 3.63 g (31% of theory) of the above ester are obtained. Analysis for $C_{13}H_{14}O_4$: calculated C 66.66%, H 6.03%, O 27.32%; found C 66.07%, H 5.97%, O 27.08%.

EXAMPLE 63

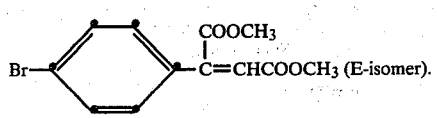

This compound is prepared from 10.97 g (50 millimols) of bromobenzoyl chloride and 9.01 g (62.5 millimols) of dimethyl maleate; the mixture is stirred for 5 hours at 120° C. The crude product is distilled in vacuo. 4.36 g (31% of theory) of the above compound (distilling at 122° C./13.3 Pa) are obtained as a yellow liquid. Analysis for $C_{12}H_{11}BrO_4$: calculated C 48.19%, H 3.71%, O 21.40%; found C 48.61%, H 3.90%, O 21.25%.

EXAMPLE 64

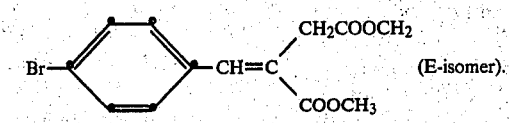

This compound is prepared analogously to Example 63, except that 9.88 g (62.5 millimols) of dimethyl itaconate are used and the reaction mixture is stirred for 3¼ hours at 120° C. After distillation of the crude product in vacuo, 8.2 g (53% of theory) of the abovecompound are obtained as a yellow liquid (which distils at 143°–50° C./13.3 Pa).

EXAMPLE 65

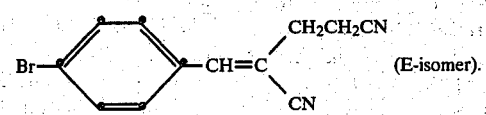

This compound is prepared analogously to Example 63, except that 6.63 g (62.5 millimols) of 2-methyleneglutarodinitrile are used and the reaction mixture is stirred for 2¼ hours at 120° C. The crude product is distilled in vacuo and is subsequently recrystallised from methanol. 3.5 g (27% of theory) of the above compound are obtained as white crystals, of melting point 60.2° C. Analysis for $C_{12}H_9BrN_2$: calculated C 55.20%, H 3.48%, N 10.73%; found C 55.59%, H 3.58%, N 10.48%.

EXAMPLE 66

4-Phenylcinnamonitrile (trans)

This compound is prepared from 10.83 g (50 millimols) of biphenyl-4-carboxylic acid chloride and 3.31 g (62.5 millimols) of acrylonitrile, the mixture being stirredfor 2 hours at 120° C. The crude product is extracted, in a Soxhlet extractor, with 100 ml of n-hexane, and is recrystallised from methanol. 3.83 g (37% of theory) of yellow crystals, melting point 43.7° C., are obtained. Analysis for $C_{15}H_{11}N$: calculated C 87.77%, H 5.40%, N 6.82%; found C 87.64%, H 5.34%, N 6.76%.

EXAMPLE 67

4-Phenylcinnamic acid N,N-diethylamide (trans)

This compound is prepared from 10.83 g (50 millimols) of biphenyl-4-carboxylic acid chloride and 7.94 g (62.5 millimols) of N,N-diethylacrylamide, the mixture being stirred for 50 minutes at 120° C. The crude product is extracted, in a Soxhlet extractor, with 125 ml of n-hexane, and is recrystallised once from diethyl ether. 8.5 g (15% of theory) of pale yellow crystals, melting point 113.3° C., are obtained. Analysis for $C_{10}H_{21}NO$: calculated C 81.72%, H 7.53%, N 5.02%; found C 81.44%, H 7.50%, N 4.91%.

EXAMPLE 68

3,4-Dimethylcinnamonitrile 0.448 g (2 millimols) of palladium acetate, 33.7 g (0.2 mol) of 3,4-dimethylbenzoyl chloride, 13.25 g (0.25 mol) of acrylonitrile and 37.06 g (0.2 mol) of tri-n-butylamine in 200 ml of p-xylene are stirred for 1.5 hours at 120° C. The mixture is then extracted by shaking with 200 ml of 2 N HCl, 200 ml of 2 N NaOH and 100 ml of water, after which it is dried for 15 minutes with 20 g of magnesium sulfate. The crude product is chromatographed on silica gel in methylene chloride, and is recrystallised from n-hexane. 10.0 g (32% of theory) of 3,4-dimethylcinnamonitrile are obtained as pale yellow crystals, melting point 93.9° C. Analysis for $C_{11}H_{11}N$: calculated C 84.04%, H 7.05%, N 8.91%; found C 83.65%, H 6.87%, N 9.03%.

The following compounds are prepared substantially by the procedure described in Example 68:

EXAMPLE 69

3,4-Dimethylcinnamic acid N,N-diethylamide

This compound is prepared from 31.75 g (0.25 millimol) of N,N-diethylacrylamide, the mixture being stirred for 2 hours at 120° C. The crude product is distilled in vacuo and then recrystallised from n-hexane. 13.3 g (29% of theory) of the above compound are obtained in the form of white crystals, of melting point 36.6° C. Analysis for $C_{15}H_{21}NO$: calculated C 77.88%, H 9.15%, N 6.06%; found C 77.22%, H 8.93%, N 6.01%.

EXAMPLE 70

Ethyl 3,4-dimethylcinnamate

This compound is prepared from 27.08 ml (0.2 mol) of ethyl acrylate, the mixture being stirred for 2 hours at 120° C. The crude product is distilled at 125°–128° C./173 Pa. 12.72 g (62% of theory) of a colourless liquid are obtained. Analysis for $C_{13}H_{16}O_2$: calculated C 76.44%, H 7.90%, O 15.67%; found C 76.79%, H 8.22%, O 15.88%.

EXAMPLE 71

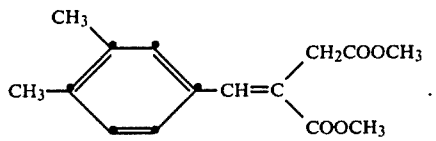

This compound is prepared from 31.6 g (0.2 mol) of dimethyl itaconate and 27.04 g (0.2 mol) of N-benzyldimethylamine, the mixture being stirred for 4 hours at 130° C. The crude product is chromatographed on silica gel in methylene chloride and is then distilled in vacuo. 23.1 g (44% of theory) of a yellow liquid are obtained. Analysis for $C_{15}H_{18}O_4$: calculated C 68.69%, H 6.92%, O 24.40%; found C 68.9%, H 6.8%, O 24.4%.

EXAMPLE 72

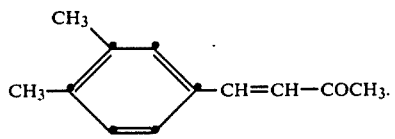

This compound is prepared from 14.18 g (0.2 mol) of vinyl methyl ketone and 27.04 g (0.2 mol) of N-benzyldimetylamine, the mixture being stirred for 1.5 hours at 130° C. The crude product is chromatographed on silica gel, using methylene chloride, and is then recrystallised from n-hexane. 3.2 g (9% of theory) of yellow crystals are obtained.

EXAMPLE 73

3,4-Dichlorocinnamonitrile

This compound is prepared from 41.89 g (0.2 mol) of 3,4-dichlorobenzoyl chloride, the mixture being stirred for 2 hours at 120° C. The crude product is chromatographed on silica gel, using methylene chloride, and is then recrystallised from n-hexane. 7.3 g (24% of theory) of pale yellow crystals, of melting point 98.2° C., are obtained. Analysis for $C_9H_5Cl_2N$: calculated C 54.58%, H 2.55%, N 7.07%; found C 54.5%, H 2.6%, N 7.6%.

EXAMPLE 74

3,4-Dichlorocinnamic acid N,N-diethylamide

This compound is prepared analogously to Example 73, except that 31.75 g (0.2 mol) of N,N-diethylacrylamide are used and the reaction mixture is stirred for 50 minutes at 120° C. The crude product is distilled in vacuo and then recrystallisedfrom diethyl ether/n-hexane. 18.4 g (34% of theory) of white crystals are obtained. melting point 60.7° C. Analysis for $C_{13}H_{15}Cl_2NO$: calculated C 57.37%, H 5.56%, N 5.15%, Cl 26.05%; found C 57.45%, H 5.70%, N 5.11%, Cl 25.94%.

EXAMPLE 75

Ethyl 3,4-dichlorocinnamate

This compound is prepared analogously to Example 73, except that 20.02 g (0.2 mol) of ethyl acrylate and 27.04 g (0.2 mol) of N-benzyldimethylamine are used and the reaction mixture is stirred for 40 minutes at 130° C. The crude product is extracted with 300 ml of n-pentane ina Soxhlet extractor and is then recrystallised from methanol. 25.4 g (52% of theory) of white crystals, of melting point 56° C., are obtained. Analysis for $C_{11}H_{10}O_2Cl_2$: calculated C 53.90%, H 4.11%, O 13.05%, Cl 28.93%; found C 53.77%, H 3.95%, O 13.24%, Cl 29.00%.

EXAMPLE 76

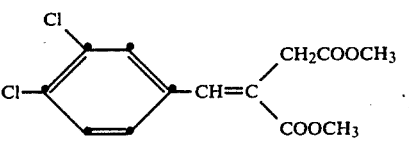

This compound is prepared analogously to Example 73, except that 31.6 g (0.2 mol) of dimethyl itaconate and 27.04 g (0.2 mol) of N-benzyldimethylamine are used, and the reaction mixture is stirred for 1.5 hours at 130° C. The crude product is distilled in vacuo at 150°–58° C./77 Pa. 28.3 g (47% of theory) of a yellow liquid are obtained. Analysis for $C_{13}H_{12}Cl_2O_4$: calculated C 51.51%, H 3.99%, O 21.11%; found C 51.18%, H 4.00%, O 21.27%.

EXAMPLE 77

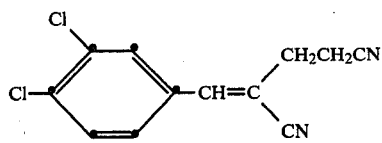

This compound is prepared analogously to Example 73, except that 21.2 g (0.2 mol) of 2-methyleneglutarodinitrile and 27.04 g (0.2 mol) of N-benzyldimethylamine are used, and the reaction mixture is stirred for 2.5 hours at 130° C. The crude product is chromatographed on silica gel in methylene chloride and is then distilled in vacuo. Thereafter it is recrystallised from carbon tetrachloride/cyclohexane. 15.8 g (31% of theory) of pale yellow crystals, of melting point 55.3° C., are obtained. Analysis for $C_{12}H_8Cl_2N_2$: calculated C 57.40%, H 3.21%, N 11.16%; found C 57.63%, H 3.37%, N 11.41%.

EXAMPLE 78

2-Methyl-5-nitrocinnamonitrile 0.336 g (1.5 millimols) of palladium acetate, 29.93 g (150 millimols) of 2-methyl-5-nitrobenzoyl chloride, 9.94 g (187.5 millimols) of acrylonitrile and 27.80 g (150 millimols) of tri-n-butylamine, in 150 ml of p-xylene, are stirred for 80 minutes at 130°. The mixture is then extracted, and dried, as described in Example 68. The crude product is chromatographed on silica gel in toluene and is then recrystallised from carbon tetrachloride/cyclohexane. 6.3 g (22% of theory) of white crystals, of melting point 115.6° C., are obtained. Analysis for $C_{10}H_8N_2O_2$: calculated C 63.83%, H 4.29%, N 14.89%; found C 63.8%, H 4.2%, N 15.1%.

EXAMPLE 79

2-Methyl-5-nitrocinnamic acid N,N-diethylamide

This compound is prepared analogously to Example 78, except that 23.8 g (187.5 millimols) of N,N-diethylacrylamide are used and the reaction mixture is stirred for 70 minutes at 120°. The crude product is distilled in vacuo and then recrystallised from diethyl ether. 9.9 g (25% of theory) of pale yellow crystals are obtained; melting point 61.9° C. Analysis for $C_{14}H_{18}N_2O_3$: calculated C 64.11%, H 6.92%, N 10.68%; found C 64.08%, H 7.04%, N 10.53%.

EXAMPLE 80

Ethyl 2-methyl-5-nitrocinnamate

This compound is prepared analogously to Example 78, except that 20.31 ml (187.5 millimols) of ethyl acrylate are used and the reaction mixture is stirred for 90 minutes at 120° C. The crude product is extracted with 270 ml of cyclohexane in a Soxhlet extractor and is then chromatographed on silica gel in methylene chloride and subsequently recrystallised from diethyl ether/ethanol. 9.24 g (39.3% of theory) of pale yellow crystals, of melting point 44.0° C., are obtained. Analysis for $C_{12}H_{13}NO_4$: calculated C 61.27%, H 5.57%, N 5.96%, O 27.21%; found C 61.29%, H 5.52%, N 6.02%, O 26.96%.

EXAMPLE 81

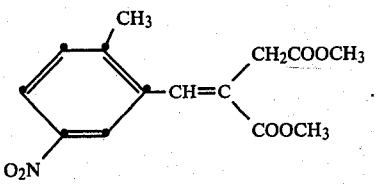

This compound is prepared analogously to Example 78, except that 24.93 g (125 millimols) of dimethyl itaconate and 23.17 g (125 millimols) of tri-n-butylamine are used, and the reaction mixture is stirred for 1 hour at 130° C. The crude product is distilled in vacuo. 11.4 g (31% of theory) of a yellow liquid (which distils at 184°–88° C./93 Pa) are obtained. Analysis for $C_{14}H_{15}O_6N$: calculated C 57.34%, H 5.16%, N 4.78%; found C 56.99%, H 5.11%, N 4.85%.

EXAMPLE 82

2-Methyl-3-nitrocinnamonitrile

This compound is prepared analogously to Example 78, except that 29.93 g (150 millimols) of 2-methyl-3-nitrobenzoyl chloride are used and the reaction mixture is stirred for 1¾ hours at 120° C. The crude product is chromatographed on silica gel in chloroform and is then recrystallised from carbon tetrachloride. 10.2 g (27% of theory) of pale yellow crystals, of melting point 135.8° C., are obtained. Analysis for $C_{10}H_8N_2O_2$: calculated C 63.83%, H 4.29%, N 14.89%; found C 63.51%, H 4.15%, N 14.89%.

EXAMPLE 83

2-Methyl-3-nitrocinnamic acid N,N-diethylamide

This compound is prepared analogously to Example 82, except that 23.81 g (187.5 millimols) of N,N-diethylacrylamide are used and the mixture is stirred for 45 minutes at 120° C. The crude product is distilled in vacuo and recrystallised from diethyl ether. 16.6 g (42% of theory) of white crystals, of melting point 74.3° C., are obtained. Analysis for $C_{14}H_{18}N_2O_3$: calculated C 64.11%, H 6.92%, N 10.68%; found C 64.63%, H 7.04%, N 10.68%.

EXAMPLE 84

Ethyl 2-methyl-3-nitrocinnamate

This compound is prepared analogously to Example 82, except that 20.31 ml (187.5 millimols) of ethyl acrylate are used, and the reaction mixture is stirred for 1.5 hours at 120° C. The crude product is recrystallised once from diethyl ether and once from n-hexane. 12.9 g (55% of theory) of pale yellow crystals, of melting point 58.2° C., are obtained. Analysis for $C_{12}H_{13}NO_4$: calculated C 61.27%, H 5.57%, N 5.96%, O 27.21%; found C 61.39%, H 5.67%, N 5.96%, O 27.33%.

EXAMPLE 85

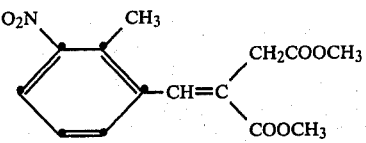

This compound is prepared analogously to Example 82, except that 23.70 g (150 millimols) of dimethyl itaconate and 17.25 g (150 millimols) of N-ethylmorpholine are used, and the reaction mixture is stirred for 1 hour at 130° C. The crude product is extracted in a Soxhlet extractor and recrystallised from n-pentane. 23.4 g (53% of theory) of pale yellow crystals, of melting point 68.4° C., are obtained. Analysis for $C_{14}H_{15}NO_6$: calculated C 57.34%, H 5.16%, N 4.78%; found C 57.30%, H 5.32%, N 4.91%.

EXAMPLE 86

3,5-Dimethoxycinnamonitrile

This compound is prepared analogously to Example 68, except that 40.1 g (0.2 mol) of 3,5-dimethoxybenzoyl chloride are used and the reaction mixture is stirred for 2¼ hours at 120° C. the crude product is chromatographed on silica gel and then recrystallised from cyclohexane. 12.2 g (32% of theory) of white crystals, of melting point 125.7° C., are obtained. Analysis for $C_{11}H_{11}NO_2$: calculated C 69.83%, H 5.86%, O 7.40%; found C 69.6%, H 5.8%, N 7.2%.

EXAMPLE 87

3,5-Dimethoxycinnamic acid N,N-diethylamide

This compound is prepared analogously to Example 86, except that 31.76 g (0.25 mol) of N,N-diethylacrylamide are used and the reaction mixture is stirred for 80 minutes at 120° C. The crude product is distilled in vacuo. 10.0 g (39% of theory) of a yellow liquid (which distilsat 188°–192° C./27 Pa) are obtained. Analysis for $C_{15}H_{21}NO_3$: calculated C 68.41%, H 8.04%, N 5.32%; found C 67.49%, H 8.30%, N 5.16%.

EXAMPLE 88

Ethyl 3,5-dimetoxycinnamate

This compound is prepared analogously to Example 86, except that 27.08 ml (0.2 mol) of ethyl acrylate are used, and the reaction mixture is stirred for 2 hours at 120° C. The crude product is distilled in vacuo. 39.6 g (84% of theory) of a colourless liquid (which distils at 150°–51° C./133 Pa) are obtained. Analysis for $C_{13}H_{16}O_4$: calculated C 66.09%, H 6.83%, O 27.09%; found C 66.21%, H 6.73%, O 27.20%.

EXAMPLE 89

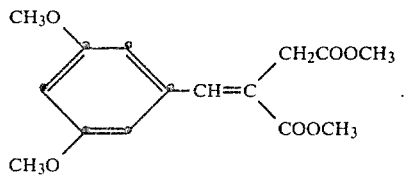

This compound is prepared analogously to Example 86, except that 31.6 g (0.2 mol) of dimethyl itaconate and 27.04 g (0.2 mol) of N-benzyldimethylamine are used, and the reaction mixture is stirred for 70 minutes at 130° C. After distilling the crude product, 38.4 g (65% of theory) of the above compound are obtained as a yellow liquid (which distils at 147°–150° C./13 Pa). Analysis for $C_{15}H_{20}O_6$: calculated C 60.80%, H 6.81%, O 32.40%; found C 61.03%, H 6.31%, O 32.82%.

EXAMPLE 90

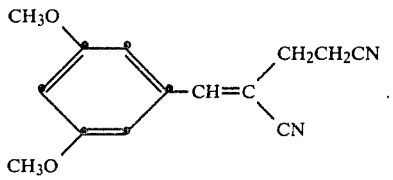

This compound is prepared analogously to Example 86, except that 21.2 g (0.2 mol) of 2-methyleneglutaronitrile and 27.04 g (0.2 mol) of N-benzyldimethylamine are used, and the reaction mixture is stirred for 4 hours at 130° C. The crude product is distilled in vacuo and recrystallised from cyclohexane. 17.1 g (35% of theory) of the above compound are obtained in the form of white crystals, of melting point 71.6° C. Analysis for $C_{14}H_{14}N_2O_2$: calculated C 69.41%, H 5.83%, N 11.57%; found C 69.72%, H 5.86%, N 11.88%.

EXAMPLE 91

3,4,5-Trimethoxycinnamonitrile

This compound is prepared analogously to Example 68, except that 46.13 g (0.2 mol) of 3,4,5-trimethoxybenzoyl chloride are used and the reaction mixture is stirred for 1.5 hours at 120° C. The crude product is distilled in vacuo and subsequently recrystallised from diethyl ether/n-hexane. 14.3 g (33% of theory) of pale yellow crystals, of melting point 92.1° C., are obtained. Analysis for $C_{12}H_{13}NO_3$: calculated C 65.74%, H 5.98%, N 6.39%; found C 65.83%, H 6.16%, N 6.27%.

EXAMPLE 92

3,4,5-Trimethoxycinnamic acid N,N-diethylamide

This compound is prepared analogously to Example 91, except that 31.75 g (0.2 mol) of N,N-diethylacrylamide are used and the reaction mixture is stirred for 2.5 hours at 120° C. The crude product is distilled in vacuo and subsequently recrystallised from diethyl ether/dioxane. 9.4 g (16% of theory) of pale yellow crystals, of melting point 131.7° C., are obtained. Analysisfor $C_{16}H_{23}NO_4$: calculated C 65.51%, H 7.90%, N 4.78%; found C 65.43%, H 7.73%, N 4.69%.

EXAMPLE 93

Ethyl 3,4,5-trimethoxycinnamate

This compound is prepared analogously to Example 91, except that 27.08 ml (0.25 mol) of ethyl acrylate are used, and the reaction mixture is stirred for 2 hours at 120° C. The crude product is distilled in vacuo and recrystallised from n-hexane. 23.6 g (47% of theory) of white crystals, of melting point 63.4° C., are obtained. Analysis for $C_{14}H_{18}O_5$: calculted C 63.15%, H 6.81%, O 30.04%; found C 63.40%, H 6.83%, O 30.09%.

EXAMPLE 94

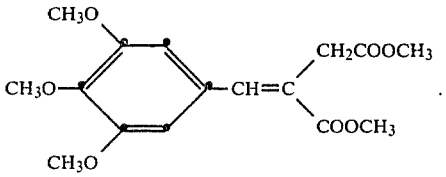

This compound is prepared analogously to Example 91, except that 31.6 g (0.2 mol) of dimethyl itaconate and 27.04 g (0.2 mol) of N-benzyldimethylamine are used, and the reaction mixture is stirred for 100 minutes at 130° C. The crude product is chromatographed on silica gel in diethyl ether and is then distilled in vacuo. 20.6 g (32% of theory) of a yellow liquid (which distils at 181°-184° C./67 Pa) are obtained. Analysis for $C_{16}H_{20}O_7$: calculated C 59.26%, H 6.22%, O 34.53%; found C 59.22%, H 6.14%, O 34.64%.

EXAMPLE 95

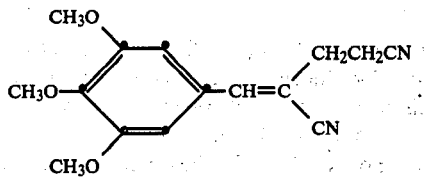

This compound is prepared analogously to Example 91, except that 21.2 g (0.2 mol) of 2-methyleneglutarodinitrile and 27.04 g (0.2 mol) of N-benzyldimethylamine are used, and the reaction mixture is stirred for 1.5 hours at 130° C. The crude product is extracted with cyclohexane in a Soxhlet extractor and is then recrystallised from methanol. 4.9 g (9% of theory) of white crystals of melting point 141.3° C., are obtained. Analysis for $C_{15}H_{16}N_2O_3$: calculated C 66.17%, H 5.92%, N 10.29%; found C 65.9%, H 6.0%, N 10.2%.

EXAMPLE 96

Ethyl pentafluorocinnamate 0.0561 g (0.25 millimol) of palladium acetate, 5.76 g (25 millimols) of pentafluorobenzoyl chloride, 2.50 g (25 millimols) of ethyl acrylate and 2.88 g (25 millimols) of N-ethylmorpholine, in 100 ml of xylene, are stirred for 6.5 hours at 130° C. The crude product is distilled in vacuo. 3.9 g (59% of theory) of a colourless liquid (which distils at 61°-64° C./12 Pa) are obtained. Analysis for $C_{11}H_7F_5O_2$: calculated C 49.64%, H 2.65%, F 35.69%; found C 49.76%, H 2.72%, F 35.90%.

EXAMPLE 97

0.1122 g ($5 \times 10^{-4}$ mols) of palladium acetate, 5.08 g ($2.5 \times 10^{-2}$ mols) of terephthalic acid dichloride, 6.78 ml ($6.25 \times 10^{-2}$ mols) of ethyl acrylate and 11.91 ml ($5 \times 10^{-3}$ mols) of tri-n-butylamine, in 100 ml of xylene, are stirred for 1 hour at 120° C. The mixture is extracted by shaking, as described in Example 48. The crude product is distilled and is recrystallised once from cyclohexane. 4.08 g (60% of theory) of white crystals, of melting point 97.1° C., are obtained. Analysis for $C_{16}H_{18}O_4$: calculated C 70.06%, H 6.62%; found C 69.89%, H 6.44%.

The compounds in Examples 98-104 are prepared analogously to Example 97.

EXAMPLE 98:

1,4-Bis-(N,N-dimethylcarbamoylvinyl)-benzene

This compound is prepared analogously to Example 97, except that 0.896 g (4 millimols) of palladium acetate, 40.6 g (0.2 mol) of terephthalic acid dichloride, 49.5 g (0.5 mol) of N,N-dimethylacrylamide and 74.12 g (0.4 mol) of tri-n-butylamine are used, and the reaction mixture is stirred for 1 hour at 120° C. The crude product is recrystallised from dioxane. 11.6 g (21% of theory) of yellow crystals, of melting point 247.0° C., are obtained. Analysis for $C_{16}H_{20}N_2O_2$: calculated C 70.56%, H 7.40%, N 10.29%; found C 70.27%, H 7.34%, N 10.10%.

EXAMPLE 99

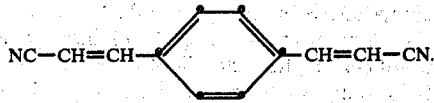

This compound is prepared analogously to Example 98, except that 26.5 g (0.5 mol) of acrylonitrile are used and the reaction mixture is stirred for 3 hours at 120° C. The crude product is extracted in a Soxhlet extractor and recrystallised from dioxane/isopropanol. 6.8 g (19% of theory) of yellow crystals are obtained. Analysis for $C_{12}H_8N_2$: calculated C 79.98%, H 4.48%, N 15.55%; found C 79.70%, H 4.68%, N 15.50%.

EXAMPLE 100

1,3-Bis-ethoxycarbonylvinylbenzene

This compound is prepared analogously to Example 98, except that 40.6 g (0.2 mol) of isophthalic acid dichloride and 50 g (0.5 mol) of ethyl acrylate are used, and the reaction mixture is stirred for 100 minutes at 120° C. The crude product is distilled in vacuo and then recrystallised from n-hexane/cyclohexane. 13.4 g (24% of theory) of white crystals, of melting point 51.5° C., are obtained. Analysis for $C_{16}H_{18}O_4$: calculated C 70.06%, H 6.62%, O 23.33%; found C 70.34%, H 6.61%, O 23.51%.

EXAMPLE 101

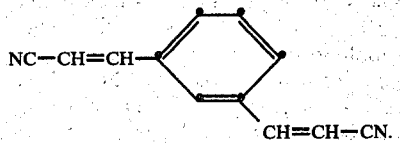

This compound is prepared analogously to Example 100, except that 26.5 g (0.5 mol) of acrylonitrile are used and the reaction mixture is stirred for 3.5 hours at 120° C. The crude product is extracted in a Soxhlet extractor and then recrystallised from cyclohexane. 2.2 g (6% of theory) of pale yellow crystals are obtained. Analysis for $C_{12}H_8N_2$: calculated C 79.98%, H 4.48%, N 14.55%; found C 79.10%, H 4.77%, N 15.28%.

EXAMPLE 102

2,6-Bis-(2-ethoxycarbonylvinyl)-naphthalene 0.1683 g (0.75 millimol) of palladium acetate, 9.49 g (37.5 millimols) of naphthalene-2,6-dicarboxylic acid dichloride, 9.38 g (93.75 millimols) of ethyl acrylate and 13.89 g (75 millimols) of tri-n-butylamine, in 150 ml of p-xylene, are stirred for 2 hours at 120° C. The crude product is chromatographed on silica gel in methylene chloride, and is then recrystallised from cyclohexane. 4.11 g (34% of theory) of yellow crystals, of melting point 150°-51° C., are obtained. Analysis for $C_{20}H_{20}O_4$: calculated C 74.06%, H 6.22%, O 19.73%; found C 73.85%, H 6.41%, O 19.56%.

EXAMPLE 103

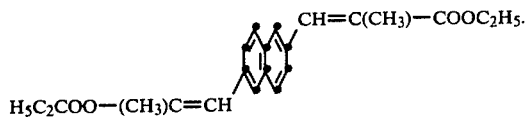

This compound is prepared from 0.0224 g (0.1 millimol) of palladium acetate, 1.27 g (5 millimols) of naphthalene-2,6-dicarboxylic acid dichloride, 1.43 g (12.5 millimols) of ethyl methacrylate and 2.31 g (12.5 millimols) of tri-n-butylamine in 20 ml of toluene, the mixture being refluxed for 3.5 hours. The crude product is extracted in a Soxhlet extractor and recrystallised from n-hexane. 0.14 g (7% of theory) of white flakes of melting point 107°-08° C. are obtained.

EXAMPLE 104

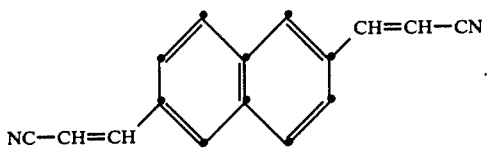

This compound is prepared analogously to Example 102, except that 4.98 g (93.75 millimols) of acrylonitrile are used and the reaction mixture is stirred for 2 hours at 120° C. The crude product is extracted in a Soxhlet extractor and then recrystallised from tetrahydrofuran/methanol. 3.12 g (30% of theory) of yellow crystals, of melting point 227°-9° C., are obtained.

EXAMPLE 105

1,4-Bis-(2-ethoxycarbonyl-vinyl)-naphthalene 0.0561 g (0.25 millimol) of palladium acetate, 3.16 g (12.5 millimols) of naphthalene-1,4-dicarboxylic acid dichloride, 3.12 g (31.25 millimols) of ethyl acrylate and 4.63 g (25 millimols) of tri-n-butylamine in 150 ml of p-xylene are stirred for 2 hours at 120° C. The crude product is chromatographed on silica gel in methylene chloride, and then recrystallised from cyclohexane. 2.31 g (57% of theory) of pale yellow crystals, of melting point 90°-91° C., are obtained. Analysis for $C_{20}H_{20}O_4$: calculated C 74.06%, H 6.22%, O 19.73%; found C 74.04%, H 6.17%, O 19.72%.

EXAMPLE 106

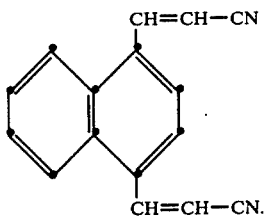

This compound is prepared analogously to Example 105, except that 1.66 g (31.25 millimols) of acrylonitrile are used and the reaction mixture is stirred for 2 hours at 120° C. The crude product is extracted with diethyl ether in a Soxhlet extractor and recrystallised from toluene/tetrahydrofuran. 0.5 g (17% of theory) of pale yellow crystals, of melting point 291°-92° C., are obtained. Analysis for $C_{16}H_{10}N_2$: calculated C 83.46%, H 4.38%, N 12.17%; found C 83.08%, H 4.44%, N 12.28%.

EXAMPLE 107

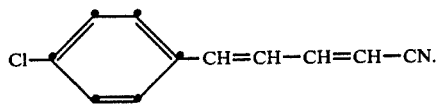

0.224 g (1 millimol) of palladium acetate, 20.1 g (100 millimols) of 4-chlorocinnamic acid chloride, 6.63 g (125 millimols) of acrylonitrile and 18.53 g (100 millimols) of tri-n-butylamine, in 100 ml of p-xylene, are stirred for 2 hours at 120° C. The crude product is chromatographed on silica gel in toluene, and is then recrystallised from n-hexane. 0.9 g (5% of theory) of yellow crystals, of melting point 83.7° C., are obtained. Analysis for $C_{11}H_8ClN$: calculated C 69.66%, H 4.25%, N 7.38%; found C 69.92%, H 4.24%, N 7.49%.

EXAMPLE 108

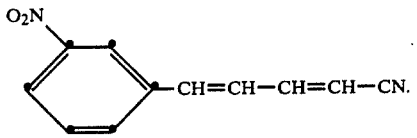

0.112 g (0.5 millimol) of palladium acetate, 10.58 g (50 millimols) of 3-nitrocinnamyl chloride, 3.31 g (62.5 millimols) of acrylonitrile and 9.27 g (50 millimols) of tri-n-butylamine in 50 ml of p-xylene, are stirred for 2 hours at 120° C. The crude product is chromatographed on silica gel in toluene and is then recrystallised from carbon tetrachloride. 3.6 g (36% of theory) of pale yellow crystals, of melting point 107.1° C., are obtained. Analysis for $C_{11}H_8N_2O_2$: calculated C 66.00%, H 4.03%, N 14.00%; found C 65.69%, H 3.93%, N 14.05%.

EXAMPLE 109

1-(2-Ethoxycarbonyl)-vinylnaphthalene 0.2244 g ($10^{-3}$ mols) of palladium acetate, 15.05 g (0.1 mol) of naphthalene-1-carboxylic acid chloride, 13.54 ml (0.125 mol) of ethyl acrylate and 23.95 ml (0.1 mol) of tri-n-butylamine, in 200 ml of p-xylene, are stirred for 1 hour at 120° C. The crude product is distilled in vacuo. 15.6 g (69% of theory) of a colourless liquid (which distils at 143°-147° C./106 Pa) are obtained. Analysis for $C_{15}H_{14}O_2$: calculated C 79.62%, H 6.24%, O 14.14%; found C 79.24%, H 6.39%, O 14.27%.

EXAMPLE 110

The amounts of palladium acetate shown below, together with 5.77 ml (50 millimols) of benzoyl chloride, 5.42 ml (50 millimols) of ethyl acrylate and 7.53 ml (50 millimols) of N-benzyldimethylamine are stirred, in 100 ml of p-xylene, for 1.5-6 hours at 130° C.

The yields of ethyl cinnamate are shown in Table 1.

TABLE 1

| Palladium acetate, mol %[1] | Reaction time h | Yield % of theory | Conversion index[2] |
|---|---|---|---|
| 0.05 | 1.5 | 80 | 1,600 |
| 0.02 | 2 | 76 | 3,800 |
| 0.01 | 2.5 | 70 | 7,030 |
| 0.005 | 6 | 53 | 10,580 |

[1] based on benzoyl chloride

[2] conversion index = mols of product formed / mols of catalyst employed

EXAMPLE 111

The amounts of palladium acetate shown in Table 2 below, 6.74 g (40 millimols) of 4-formylbenzoyl chloride, 2.63 ml (40 millimols) of acrylonitrile and 5.12 ml (40 millimols) of N-ethylmorpholine, in 80 ml of p-xylene, are stirred for 5 hours at 120° C. The yields of 4-formylcinnamonitrile are shown in Table 2.

TABLE 2

| Palladium acetate mol % | Yield % of theory | Conversion index |
|---|---|---|
| 0.1 | 84 | 840 |
| 0.04 | 64 | 1,600 |
| 0.033 | 74 | 2,200* |
| 0.02 | 31 | 1,550 |
| 0.01 | 10 | 1,000 |

*with 44 millimols of acrylonitrile in 12 hours.

EXAMPLE 112

0.095 g ($2.5 \times 10^{-4}$ mols) of diacetato-bipyridylpalladium(II), 2.88 ml (25 millimols) of benzoyl chloride, 3.39 ml (31.25 millimols) of ethyl acrylate and 5.96 ml (25 millimols) of tri-n-butylamine in 50 ml of p-xylene, are stirred for 3 hours at 120° C. Working up as described in the preceding examples affords 3.78 g (86% of theory) of ethyl cinnamate.

EXAMPLE 113

3.91 mg ($1.6 \times 10^{-5}$ mols) of palladium acetate, 6.74 g (40 millimols) of 4-formylbenzoyl chloride, 2.63 ml (40 millimols) of acrylonitrile and 4.41 ml (40 millimols) of N-methylmorpholine, in 80 ml of p-xylene, are stirred for 5 hours. Working up as described in the preceding examples affords 0.53 g (8% of theory) of 4-formylcinnamonitrile.

EXAMPLE 114

Ethyl cinnamate is prepared by the procedures described above, using different bases and the following reactants: 2.24 mg ($10^{-5}$ mols) of palladium acetate, 5.77 ml (50 millimols) of benzoyl chloride, 5.42 ml (50 millimols) of ethyl acrylate and 50 millimols of N-benzyldiethylamine or N-(3-chlorobenzyl)-dimethylamine, in 100 ml of p-xylene. The reaction mixture is stirred for 4 hours at 130° C. Ethyl cinnamate is obtained in a yield of 67% of theory if N-benzyldiethylamine is used, and a yield of 56% of theory if N-(3-chlorobenzyl)-dimethylamine is used.

EXAMPLE 115

0.2877 g (0.5 millimol) of bis-(dibenzylideneacetone)-palladium(O), 9.98 g (50 millimols) of 2-methyl-5-nitrobenzoyl chloride, 3.31 g (62.5 millimols) of acrylonitrile and 17.68 g (50 millimols) of tris-(2-ethylhexyl)-amine, in 100 ml of cyclopentanone, are stirred for 1.5 hours at 100° C. The crude product is chromatographed on silica gel, in methylene chloride, and is then recrystallised from cyclohexane/carbon tetrachloride. 2.1 g (24% of theory) of 2-methyl-5-nitrocinnamonitrile are obtained in the form of white crystals; melting point 113.2° C.

EXAMPLE 116

0.152 g (0.5 millimol) of bis-(acetylacetonato)palladium(II), 10.53 g (50 millimols) of 3,4-dichlorobenzoyl chloride, 7.5 g (75 millimols) of ethyl acrylate and 17.65 g (50 millimols) of tri-n-octylamine in 100 ml of diethyl oxalate are stirred for 2.5 hours at 120° C. The crude product is distilled in vacuo and then recrystallised from methanol. 1.4 g (11% of theory) of ethyl 3,4-dichlorocinnamate are obtained; melting point 56.0° C.

EXAMPLE 117

0.0792 g (5 millimols) of palladium(II) cyanide, 10.03 g (50 millimols) of 3,5-dimethoxybenzoyl chloride, 6.26 g (62.5 millimols) of ethyl acrylate and 6.46 g (50 millimols) of N-ethyldiisopropylamine, in 100 ml of benzonitrile, are stirred for 70 minutes at 140° C. The crude product is distilled in vacuo. Working up affords 5.83 g (49% of theory) of ethyl 3,5-dimethoxycinnamate as a colourless liquid.

EXAMPLE 118

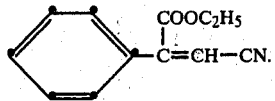

3.51 g (25 millimols) of benzoyl chloride, 3.13 g (25 millimols) of ethyl β-cyanoacrylate and 3.38 g (25 millimols) of N-benzyldimethylamine are added to 0.0561 g (0.25 millimol) of palladium acetate in 50 ml of p-xylene under argon, and the mixture is stirred for 7 hours at 130° C. The crude product is distilled in vacuo; boiling point 92°–107° C./13 Pa. 2.3 g (46% of theory) of a mixture of the E-isomer and Z-isomer of ethyl cinnamonitrile-β-carboxylate are obtained.

EXAMPLE 119

0.0018 g (0.008 millimol) of palladium acetate, 6.74 g (40 millimols) of 4-formylbenzoyl chloride, 3.29 g (50 millimols) of acrylonitrile and 5.12 ml (40 millimols) of N-ethylmorpholine are added to 80 ml of anisole. The mixture is stirred for 12 hours at 120° C., under argon. The crude product is distilled in vacuo and is then recrystallised from isopropanol. 3.2 g (52% of theory) of 4-formylcinnamonitrile are obtained in the form of white crystals.

EXAMPLE 120

54.88 g (0.25 mol) of 4-bromobenzoyl chloride, 20.81 ml (0.31 mol) of acrylonitrile and 37.65 ml (0.25 mol) of N-benzyldimethylamine are added to 0.561 g (2.5 millimols) of palladium acetate in 500 ml of p-xylene. The mixture is stirred for 1.5 hours at 120° C. The crude product is distilled and recrystallised from cyclohexanone. 35 g (67% of theory) of 4-bromocinnamonitrile are obtained in the form of white flakes; melting point 105.7° C. Analysis for $C_9H_4NBr$: calculated C 51.96%, H 2.91%, N 6.73%, Br 38.40%; found C 51.93%, H 3.01%, N 6.69%, Br 38.35%.

EXAMPLE 121

Using various catalysts, ethyl cinnamate is prepared as follows, in accordance with the procedure described in the preceding examples: 0.1 g of palladium metal or 0.25 millimol of one of the catalysts listed below, 2.89 ml (25 millimols) of benzoyl chloride, 2.71 ml (25 millimols) of ethyl acrylate and 3.77 ml (25 millimols) of N-benzyldimethylamine are added to 50 ml of p-xylene, under argon, and the reaction mixture is stirred for 2 hours at 130° C. After working up, ethyl cinnamate is obtained in the yields shown below.

| Catalyst | Yield |
|---|---|
| 0.0613 g (0.25 millimol) of [Pd(NH$_3$)$_4$]Cl$_2$ | 80% of theory |
| 0.081 g (0.25 millimol) of bis-(cyclohexlisonitrile)-palladium(O) | 80% of theory |
| 0.0833 g (0.25 millimol) of PdCl$_2$[OS(CH$_3$)$_2$]$_2$ | 69% of theory |
| 0.0958 g (0.25 millimol) of PdCl$_2$(NC—phenyl)$_2$ | 78% of theory |
| 0.1 g of palladium metal | 9% of theory |

What is claimed is:

1. A process for the preparation of a compound of the formula I

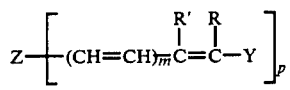  (I)

in which m is zero or 1, p is 1 or 2, Z is substituted or unsubstituted phenyl or naphthyl if p=1, and substituted or unsubstituted phenylene or naphthylene if p=2, R is hydrogen, C$_{1-4}$-alkyl, —CH$_2$COOR'' or —CH$_2$CH$_2$CN and R' is hydrogen, or, if p=1 and m=zero, can also be C$_{1-4}$-alkyl, —CN or —COOR'', but at least one of R and R' must be hydrogen, Y is —CN, —COOR'', —CON(R'')$_2$ or —COR'' and the radicals R'', independently of one another, are C$_1$-C$_{12}$-alkyl or phenyl, which comprises reacting a compound of the formula II

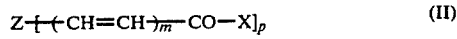  (II)

in which Z, m and p are as defined for formula I and X is chlorine, bromine or iodine, with a compound of the formula III or if desired, where p=2, with a mixture of two different compounds of the formula III

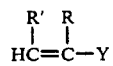  (III)

in which R, R' and Y are as defined for formula I, in the presence of a base and with the addition, as a catalyst, of palladium metal or of a palladium compound which under the reaction conditions forms a phosphorus-free labile palladium(O) compound.

2. A process according to claim 1, wherein a compound of the formula II, in which X is clorine, is used.

3. A process according to claim 1, wherein the palladium compound used in PdCl$_2$, PdBr$_2$, Pd(OOCCH$_3$)$_2$, 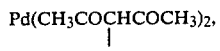 Pd(OOCCH$_3$)$_2$(2,2'-bipyridyl), PdCl$_2$(NC-phenyl)$_2$, bis-(dibenzylidene-acetone)-palladium(O) or bis-(cyclohexylisonitrile)-palladium(O).

4. A process according to claim 1, wherein the palladium compound used is PdCl$_2$, palladium acetate or bis-(dibenzylidene-acetone)-palladium(O).

5. A process according to claim 1, wherein the reaction is carried out at a temperature of between 0° and 200° C. and in the presence of an organic solvent which is inert towards the reactants.

6. A process according to claim 5, wherein the solvent used is anisole, a xylene, or toluene.

7. A process according to claim 1, wherein the base used is a compound of the formula VI

in which Q$_5$ is 4-chlorobenzyl, 3-methylbenzyl, 3-methoxybenzyl or benzyl and Q$_6$ and Q$_7$ are each alkyl having 1-4 C atoms, or in which Q$_5$, Q$_6$ and Q$_7$ are each alkyl having 3-12 C atoms.

8. A process according to claim 1, wherein the base used is N-benzyldimethylamine, N-ethylmorpholine or tri-n-butylamine.

9. A process according to claim 1, wherein the amount of catalyst used is from 0.001 to 3 mol %, based on the compound of the formula II.

10. A process according to claim 1, wherein the acid halide used is a compound of the formula IIa, IIb or IIc

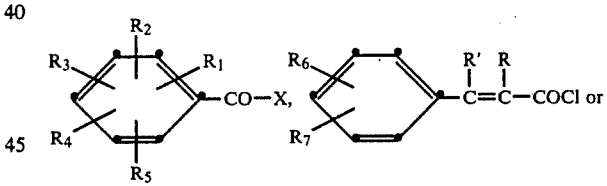

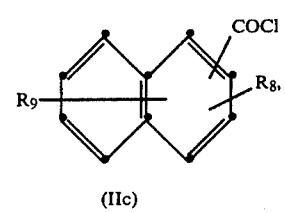

in which X is chlorine, one of R and R' is hydrogen and the other is hydrogen or methyl, or R is hydrogen and R' is —COO-alkyl having 1-4 C atoms in the alkyl moiety, R$_1$ is hydrogen, Cl, Br, F, I, formyl, methyl, methoxy, chloromethyl, cyano, nitro, —OCOCH$_3$, —COOCH$_3$ or phenyl, R$_2$ is hydrogen, Cl, F, methyl or methoxy, R$_3$ is hydrogen, Cl, F or methoxy and R$_4$ and R$_5$ are each hydrogen, or, if R$_1$, R$_2$ and R$_3$ are Cl or F, are also Cl or F, R$_6$ is hydrogen, chlorine or nitro, R$_7$ is hydrogen, R$_8$ is methyl and especially hydrogen and R$_9$ is hydrogen, or the acid halide used is isophthalic acid dichloride, terephthalic acid dichloride, 1,4-naphthalenedicarboxylic acid dichloride or 2,6-naphthalenedicarboxylic acid dichloride.

11. A process according to claim 1, wherein a compound of the formula III is used, in which R and R' are hydrogen and Y is —CN, —COR", —COOR" or —CON(R")$_2$, each R" being methyl or ethyl, or R is hydrogen, R' is methyl and Y is —CN, —COOCH$_3$, —COOC$_2$H$_5$, —CON(CH$_3$)$_2$ or —CON(C$_2$H$_5$)$_2$, or R is hydrogen and R' and Y are ech —CN, —COOCH$_3$ or —COOC$_2$H$_5$, or R' is hydrogen, R is methyl and Y is —CN, —COOCH$_3$, —COOC$_2$H$_5$, —CON(CH$_3$)$_2$ or —CON(C$_2$H$_5$)$_2$, or R' is hydrogen, R is —CH$_2$COOCH$_3$ and Y is —COOCH$_3$, or R' is hydrogen, R is —CH$_2$CH$_2$CN and Y is —CN.

12. A process according to claim 1, wherein 4-formylbenzoyl chloride, 4-bromobenzoyl chloride or especially benzoyl chloride is used as the compound of the formula II and ethyl acrylate, acrylonitrile or N,N-diethylacrylamide is used as the compound of the formula III.

* * * * *